United States Patent [19]

Lyons et al.

[11] 4,132,742

[45] Jan. 2, 1979

[54] PROCESS FOR MAKING CODIMERS OF NORBORNADIENE AND PHENYLACETYLENES USING A COBALT CATALYST

[75] Inventors: James E. Lyons, Wallingford; Abraham Schneider, Overbrook Hills; Harry K. Myers, Jr., Aston, all of Pa.

[73] Assignee: Suntech, Inc., Wayne, Pa.

[21] Appl. No.: 842,813

[22] Filed: Oct. 17, 1977

[51] Int. Cl.² ................... C07C 13/28; C07C 18/12
[52] U.S. Cl. ................... 260/668 A; 260/666 PY; 149/109.4; 149/109.6
[58] Field of Search ................... 260/666 PY, 668 F; 149/109.4, 109.6

[56] References Cited

U.S. PATENT DOCUMENTS 3,978,147    8/1976    Wilke et al. ................... 260/666 PY

OTHER PUBLICATIONS

T. Mitsudo et al., J. Chem. Soc. Chem. Comm., pp. 722-723, 1976.
M. Hara et al., Tetrahedron, pp. 96-100, 1966.
A. Carbonavo et al., Tetrahedron Letters, 49, pp. 5129-5130, 1965.
T. Sasaki et al., J. Org. Chem. 37, No 14, 1972.
Schrauzer et al., Chem. Ber. 97, pp. 2451-2462, 1964.

Primary Examiner—Veronica O'Keefe
Attorney, Agent, or Firm—J. Edward Hess; Donald R. Johnson; Anthony Potts, Jr.

[57] ABSTRACT

Novel codimers (I) of norbornadiene and phenylacetylenes and their hydrogenated derivatives (II), having the following structures

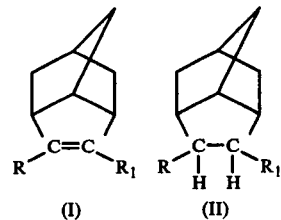

wherein R is a hydrogen, a phenyl, or a phenyl having alkyl substituents and $R_1$ is a phenyl or a phenyl having alkyl substituents and processes for preparing both are disclosed. Codimer (II) can be used as a high energy fuel or a diluent for such a fuel. Process for making codimer (I) involves reacting norbornadiene and phenylacetylene or diphenylacetylene with a catalyst system of cobaltic or cobaltous acetylacetonate, 1,2-bis-diphenylphosphino ethane and an alkyl aluminum chloride.

11 Claims, No Drawings

PROCESS FOR MAKING CODIMERS OF NORBORNADIENE AND PHENYLACETYLENES USING A COBALT CATALYST

BACKGROUND OF THE INVENTION

The invention herein described was made in the course of or under a contract thereunder with the United States Air Force Systems Command.

CROSS REFERENCES TO RELATED APPLICATIONS

This application is related to U.S. Application Ser. No. 842,812 filed at the same time by the above-identified inventors. Subject matter of related application is the reaction of norbornadiene and an alkyne.

The invention relates to the catalytic codimerization of norbornadiene and phenylacetylenes or diphenylacetylenes. Particularly the invention relates to the preparation of an olefinic codimer of norbornadiene and phenylacetylenes or diphenylacetylenes using a specified catalyst system. Hydrogenation of either of the resulting olefinic codimers yields a saturated codimer having utility as a high energy fuel or a diluent for such fuels. The phenylacetylenes and diphenylacetylenes are referred to hereinafter collectively as PACE.

High energy fuel, which is often referred to as a high density fuel, can be used in either jet or rocket propulsion. Jet propulsion includes a jet engine which can be used for a missile plane and others and includes the three basic types, i.e., ramjet, turbo-jet and pulse jet. The term rocket generally refers to a device containing its own oxygen or oxidizing agent.

Norbornadiene is also known as bicyclo-(2.2.1) heptadiene-2,5. A method of preparation is disclosed in U.S. Pat. No. 2,875,256 issued Feb. 24, 1959. Hereinafter, norbornadiene is referred to as NBD. The latter can be represented by either one of the following structural formulas:

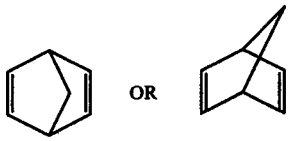

NBD can be easily dimerized to an exo-exo hexacyclic dimer. Thus one problem in reacting NBD with another hydrocarbon reactant is to minimize the formation of the homodimer while encouraging the formation of the desired codimer.

The reaction of norbornenes and acetylenes without using a catalyst has been reported in *J.C.S. Chem. Comm.*, 1976, pages 722-723, T. Mitsudo et al, in article titled "Ruthenium-catalyzed [2 + 2] Cross addition of Norbornene Derivatives and Dimethyl Acetylene dicarboxylate". Such reactions are also reported in *Tetrahedron*, 1966, M. Hara et al, "Photo-Addition-Reactions of Dimethyl Maleate and Dimethyl Acetylene Dicarboxylate with Norbornene". A. Carbonaro, et al in *Tetrahedron Letters*, 49, 1965, pages 5129-5130 in "Oligomerization Catalysts-IV., Formation of Benzene Derivatives by Catalytic Reaction Between Norbornadiene and Acetylenic Hydrocarbons; A Core of Catalyzed Inverse Diels-Alder Reaction", reports on the formation of aromatic compounds in the presence of iron catalysts. T. Sasaki et al in an article in the *J.Org. Chem.*, Vol. 37, No. 14, 1972, titled "Studies on Reactions of Isoprenoids" reports on reactions of norbornadiene with unsymmetrically substituted acetylenic and heterodienophiles in the absence of a catalyst. Schrauzer et al in an article titled "Catalytic Addition of Olefins and Alkynes to Norbornadiene with $Ni^0$ compounds and a New $Ni^{II}$ complex as Catalyst", in *Jahrg.* 97, 1964, pages 2451-2462, reports on reactions or norbornadiene with diphenylacetylene or acetylene.

SUMMARY OF THE INVENTION

Novel codimer I of NBD and PACE having the following structure:

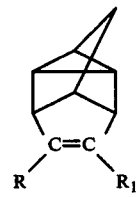

(I)

wherein R is a hydrogen, phenyl or a phenyl having alkyl substituents, and $R_1$ is a phenyl or a phenyl having alkyl substituents, can be prepared by contacting NBD and PACE in the presence of a catalytic amount of a homogeneous catalytic system of cobaltic or cobaltous acetylacetonate, 1,2-bisdiphenylphosphino ethane, and one of three alkyl aluminum chlorides. Resulting codimer I can be hydrogenated and then used as a high energy fuel or as a diluent for such a fuel. Hydrogenated product II has the structure as shown herein. The structure of the phenyl having alkyl substituents is as follows

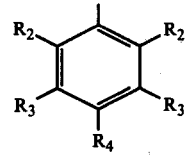

wherein $R_2$ is a hydrogen or methyl; $R_3$ is a hydrogen or a $C_1$–$C_5$ alkyl; and $R_4$ is a hydrogen or a $C_1$–$C_{10}$ alkyl.

DESCRIPTION

Cobaltic acetylacetonate ($Co(C_5H_7O_2)_3$) is referred to hereinafter as $CoA_3$ whereas the cobaltous form ($Co(C_5H_7O_2)_2$) is referred to as $CoA_2$. Collectively the two are referred to as CoA. The 1,2-bisdiphenylphosphino ethane is referred to as DIPHOS while the alkyl aluminum chloride is referred to as AAC.

The catalytic codimerization of NBD and PACE via present invention can be represented by the following formula reaction

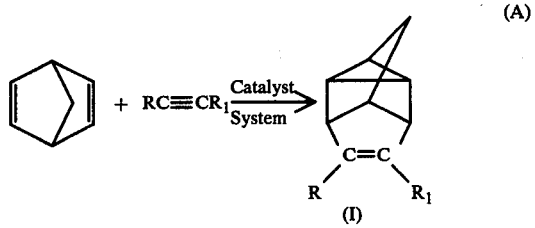

(A)

wherein R is a hydrogen, phenyl or a phenyl having alkyl substituents and R₁ is a phenyl or a phenyl having alkyl substituents. The structure of the phenyl having alkyl substituents is as follows:

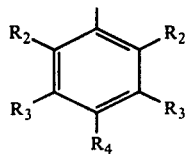

wherein $R_2$ is a hydrogen or methyl; $R_3$ is a hydrogen or a $C_1$-$C_5$ alkyl and $R_4$ is a hydrogen or a $C_1$-$C_{10}$ alkyl. As shown, NBD and PACE are contacted in the presence of a catalytic amount of the catalyst system which is defined herein.

Codimer I upon hydrogenation forms product II. The hydrogenation step can be represented by the following formula reaction

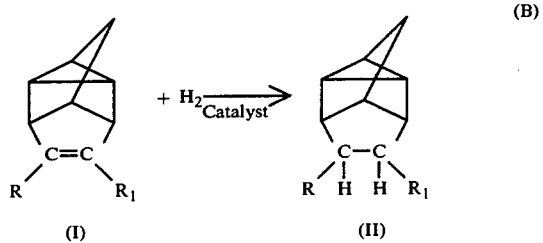

(B)

wherein R and $R_1$ are as defined herein. A hydrogenation catalyst such as $PtO_2$ can be used. The hydrogenation proceeds rapidly at reasonable temperatures.

The NBD used can contain a nominal amount of similar hydrocarbons, however, which if present should not be of a type which could adversely effect the reaction. If the NBD used contains undesirable hydrocarbons, they can be removed by known means. The foregoing also applies to the PACE used. Thus the hydrocarbons used in the invention can consist essentially of NBD and PACE.

In the codimerization of NBD and PACE one mole of each reacts with the other to form one mole of the NBD-PACE codimer II. However, if the NBD and PACE mole ratio is too large homodimerization can occur with an adverse effect on codimer yields. On the other hand, if the NBD to PACE mole ratio is too low then the yield per pass can be too low and hence uneconomical. Within the aforementioned range a preferred NBD to PACE mole ratio is in the range between from about 0.01 to about 10 with about 0.1 to about 2 more preferred.

The catalytic system favoring the aforementioned codimerization reaction A contains components which are commercially available and methods for their preparation are reported in the literature. The three are $CoA_3$ or $CoA_2$, DIPHOS and AAC. The AAC can be selected from the group consisting of diethylaluminum chloride, ethyl aluminum dichloride and ethyl aluminum sesquichloride. The latter three are referred to as DEAC, EADC and EASC, respectively. The amount of any component present is a catalytic amount so that a suitable conversion to codimer II occurs and the selectivity as to it is sufficient. Material, which during the codimerization reaction could adversely affect the catalyst system, should not be present. For example, the presence of hydroxylic compounds such as water, alcohol or oxygen from air could deactivate the catalyst system. Thus the catalytic system can consist of the aforementioned three components.

The amount of CoA present should be catalytically sufficient to obtain the desired product. Generally the NBD to CoA mole ratio can range between from about 10 to about 2000 with a preferred range between from about 20 to about 1000.

Another component of the catalyst system is DIPHOS which has the following formula: $[(C_6H_5)_2PCH_2]_2$. The amount of this component of the catalyst system should be catalytically sufficient to obtain the desired product. Generally the DIPHOS to CoA mole ratio can range between from about 0.1 to about 5 with a preferred range between from about 1 to about 4.

DEAC, EADC or EASC is another component of the catalyst system with DEAC preferred. The amount of this component can vary substantially but generally it relates to the amount of CoA used. An effective DEAC, EADC or EASC to CoA mole ratio can be between from about 0.5 to about 100 with from about 1 to about 50 preferred and from about 3 to about 20 more preferred. Generally, when DEAC, EADC or EASC is used it is advantageous to conduct the reaction under substantially anhydrous conditions and under an inert gas blanket. Excess DEAC, EADC or EASC also serves as a scavenger.

Selectivity refers to the amount, mole or weight, of a particular compound formed divided by the amount of all compounds formed. From a commercial standpoint the economics of an overall process determines the optimal levels for both the selectivity and yield.

The reaction time required for an economically satisfactory selectivity and/or yield depends on a number of factors, such as catalyst to feed ratio, as well as operating conditions. Also the economics depend on capital investment versus conversion per pass and the like. The catalyst to feed ratios are discussed herein while typical conditions are provided by the Example.

A solvent can be used in the codimerization reaction. The solvent can be inert or it can be the NBD itself. Since the reaction is mildly exothermic the solvent can serve as a heat sink. It can also assist in solubilizing the reaction components, that is the feed and the components of the catalyst, and thereby provide for a homogeneous reaction medium. Some solvent can be added to the system as a carrier for one or more of the catalyst components. For example, DEAC is often maintained in an inert solvent such as toluene rather than NBD itself. Furthermore, the solvent should not adversely react with the feed, products or catalyst, therefore, if it is not NBD, it should be inert. Also, presence of the solvent can facilitate the handling of the reaction mixture. Classes of suitable inert solvents include aromatic hydrocarbons, cycloparaffins, ethers, halogenated aromatics, halogenated paraffins and halogenated cycloparaffins. Specific examples include benzene, toluene, xylenes, cyclohexane, cyclopentane, diethylether, chlorobenzene, bromobenzene, chlorinated cyclohexane and the like. As to the amount of solvent used, excessive amounts decrease the reaction rate, and thus adversely affect the economics for a commercial operation.

The codimerization of NBD and PACE with the homogeneous catalyst system can occur at ambient temperature. Thus the temperature of the mixture of feed and homogeneous catalyst system need not be raised to initiate reaction A. However, if the mixture is at an extremely low temperature, heating of the cooled mixture could be necessary. Furthermore, once reaction A is underway, some heat is generated and the temperature of the mixture increases. If the temperature increases too much then some cooling would be required. Generally, however, the codimerization of NBD and PACE with a reasonable amount of the catalyst system is not characterized by an extremely rapid exotherm.

Selective codimerization of the NBD and PACE most efficiently occurs in a liquid phase and therefore it is not desirable to have the reaction temperature largely exceed the boiling points of the NBD and/or any solvent. Conversely, if the temperature is too low the reaction rate could be too low to be economically feasible. An operable temperature range is between from about 20° C. to about 100° C. with about 25° C. to about 85° C. a preferred range. The operating pressure can vary substantially, however, it can range from about atmospheric up to about 2000 psi with about 100 psi a preferred upper value. Process economics favor lower operating pressure, however, a moderately elevated reaction pressure may be desirable to keep the NBD in solution.

To further illustrate the invention, the following example and comparative run are provided.

EXAMPLES

The codimer of NBD and phenylacetylene was prepared in the following manner. In a suitable vessel 0.02 millimoles of CoA$_3$, 0.03 millimoles of DIPHOS and 9.8 millimoles of NBD were mixed at 24° C. and then deaerated. Then 9.1 millimoles of liquid phenylacetylene was added followed by 0.4 millimoles of DEAC (1.9 molar in toluene). The green solution became hazy brown with an immediate exotherm and vigorous boiling. Because of the exotherm the vessel was placed in a −60° C. bath. After the temporary quenching the vessel was returned to a 35° C. bath and then sampled two hours after the addition of the DEAC. The sample was quenched to deactivate the catalyst and then analyzed by vapor phase chromatography. A 17.1 mole % conversion of the NBD to the codimer was obtained along with 2.7% mole conversion to the homodimer, Binor-S. Structure of the codimer was confirmed by mass spectrometry, infrared analysis and nuclear magnetic resonance.

The codimer of NBD and diphenylacetylene was prepared in the following manner. In a suitable vessel 0.5 milliliters (0.02 millimoles) of CoA$_3$ in a 0.04 molar solution in benzene, 0.5 milliliters (0.02 millimoles) of 1,2-bisdiphenylphosphino ethane in a 0.04 molar solution in benzene, 0.51 milliliters (5 millimoles) of NBD and 1.78 grams (10 millimoles) of diphenylacetylene were mixed at 24° C. and deaerated. The resulting green solution containing some solid diphenylacetylene was then heated to a temperature of about 60° C. and held at that level for about 12–13 minutes. Then 1.0 milliliter (1 millimole) of DEAC in a 1 molar solution in benzene was added to the mixture. Upon addition of the DEAC the green solution changed to a brown solution. The resulting brown solution was maintained at a temperature of 57°–59° C. for about 330 minutes at which time the heating was discontinued. About 19–20 hours later the solution was a clear amber but showed fine particles upon agitation. A sample of the solution was taken, the catalyst was quenched and the solution then analyzed by vapor phase chromatography. Some 60.7 wt.% of the NBD was converted with a 41.9 wt.% selectivity to the codimer. Structure of the codimer of NBD and diphenylacetylene was confirmed by mass spectrometry, infrared analysis and nuclear magnetic resonance.

Analogous results will be obtained when CoA$_2$ is used in lieu of CoA$_3$ and/or DEAC is replaced by either EADC or EASC. Also analogous results will be obtained when other phenylacetylenes having or diphenylacetylenes having alkyl substituents are used in lieu of phenylacetylene or diphenylacetylene.

Either codimer can be hydrogenated to give codimers II, with hydrogen using any one of numerous hydrogenation catalysts such as PtO$_2$. The hydrogenation will proceed rapidly and selectivity to codimers II.

An attempt to prepare the codimer I using ferric acetylacetonate in lieu of CoA$_3$ and using similar operating conditions was unsuccessful.

The invention claimed is:

1. Process for the catalytic codimerization of norbornadiene with a phenylacetylene comprising:
    (a) contacting norbornadiene and phenylacetylene group having the following structure: R-C≡CR$_1$ wherein R is a hydrogen, phenyl or a phenyl having an alkyl substituent and R$_1$ is a hydrogen, phenyl or a phenyl having an alkyl substituent wherein the phenyl having alkyl substituents has the following structure:

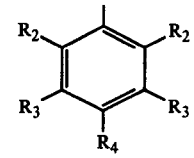

wherein R$_2$ is a hydrogen or methyl; R$_3$ is a hydrogen or C$_1$–C$_5$ alkyl; and R$_4$ is a hydrogen or C$_1$–C$_{10}$ alkyl, in the presence of a catalytic amount of a homogeneous catalytic system of cobaltic or cobaltous acetylacetonate, 1,2-bisdiphenylphosphino ethane and one of the following alkyl aluminum chlorides: diethyl aluminum chloride, ethyl aluminum dichloride and aluminum ethylsesquichloride;
    (b) having the contacting occurring at a temperature within the range from between about 20° C. to about 100° C.; and
    (c) continuing the contacting until the codimer of norbornadiene and the phenylacetylene is prepared.

2. Process according to claim 1 wherein the bisdiphenylphosphino ethane to the acetylacetonate mole ratio is in the range between from about 0.1 to about 5.

3. Process according to claim 1 wherein the norbornadiene to the acetylene mole ratio is in the range between from about 0.01 to about 10.

4. Process according to claim 1 wherein the alkyl aluminum chloride to the acetylacetonate mole ratio is in the range between from about 0.5 to about 100.

5. Process according to claim 1 wherein the norbornadiene to the acetylacetonate mole ratio is in the range between from about 10 to about 2000.

6. Process according to claim 5 wherein an inert solvent is present.

7. Process according to claim 6 wherein the inert solvent is selected from the group consisting of aromatic hydrocarbon, cycloparaffin, ether, halogenated aromatic hydrocarbon, halogenated paraffin and halogenated cycloparaffin.

8. Process according to claim 7 wherein the norbornadiene to the acetylacetonate mole ratio is in the range between from about 10 to about 2000.

9. Process according to claim 8 wherein the norbornadiene to the acetylene mole ratio is in the range between from about 0.01 to about 10.

10. Process according to claim 9 wherein the alkyl aluminum chloride to the acetylacetonate mole ratio is in the range between from about 0.5 to about 100.

11. Process according to claim 10 wherein the bisdiphenylphosphino ethane to the acetylacetonate mole ratio is in the range between from about 0.1 to about 5.

* * * * *